United States Patent
Wang et al.

(10) Patent No.: US 9,441,053 B2
(45) Date of Patent: Sep. 13, 2016

(54) ANALYTICAL METHOD FOR DETECTING SULFATED OLIGOSACCHARIDES

(71) Applicant: Scinopharm Taiwan, LTD., Shan-Hua, Tainan (TW)

(72) Inventors: ChungYao Wang, Tainan (TW); Imin Huang, Taoyuan County (TW); ChiaYen Wu, Chiayi County (TW); YungTe Chiang, Changhua County (TW); Helen Chao, Tainan (TW)

(73) Assignee: ScinoPharm Taiwan, Ltd., Shan-Hua (TW)

( * ) Notice: Subject to any disclaimer, the term of this patent is extended or adjusted under 35 U.S.C. 154(b) by 589 days.

(21) Appl. No.: 13/939,461

(22) Filed: Jul. 11, 2013

(65) Prior Publication Data

US 2015/0013438 A1    Jan. 15, 2015

(51) Int. Cl.
*G01N 30/02* (2006.01)
*C08B 37/00* (2006.01)
*G01N 30/88* (2006.01)

(52) U.S. Cl.
CPC ........... *C08B 37/0075* (2013.01); *G01N 30/02* (2013.01); *G01N 2030/8836* (2013.01); *Y10T 436/143333* (2015.01); *Y10T 436/18* (2015.01)

(58) Field of Classification Search
CPC .................. C08B 37/0075; G01N 2030/8836; G01N 30/02; G01N 30/72; G01N 30/7233; H01J 49/00; Y10T 436/143333; Y10T 436/18; Y10T 436/24; Y10T 436/255
USPC ............ 436/94, 119, 161, 173, 178; 422/70; 210/656, 198.2; 73/61.52
See application file for complete search history.

(56) References Cited

U.S. PATENT DOCUMENTS

| | | |
|---|---|---|
| 2009/0090856 A1 | 4/2009 | Grant et al. |
| 2009/0162938 A1 | 6/2009 | Laine et al. |
| 2010/0151584 A1* | 6/2010 | Parsons .............. B01D 15/1864 436/94 |

OTHER PUBLICATIONS

Naimy et al. Biochemistry, vol. 49, 2010, pp. 3743-3752.*
Huang et al. Analytical Chemistry, vol. 83, Sep. 16, 2011, pp. 8222-8229.*
Desai et al., "Substrate specificity of the Heparin Lyases from *Flavobacterium heparinum*," Nov. 1993, Archives of Biochemistry and Biophysics, vol. 306(2), pp. 461-468.
Ponnusamy, "Reverse-phase Ion-Pairing Ultra Performance Liquid Chromatography-Mass Spectrometry in Characterization and Fingerprinting of Diverse Sulfated Glycosaminoglycan Mimetics," May 2013, Virginia Commonwealth, University, pp. 1-195.
Zaia, "On-Line Separation Combined with MS for Analysis of Glycosaminoglycans," Mass spectrometry reviews, 2009, vol. 28(2), pp. 254-272.
PCT Application No. PCT/US2013/050147, International Search Report and Written Opinion, Apr. 15, 2014, 7 pages.
Doneanu, Catalin E. et al., "Analysis of Oligosaccharides Derived from Heparin by Ion-Pair Reversed-Phase Chromatography/Mass Spectrometry," *Anal. Chem.* (May 1, 2009) 81(9):3485-3499.
Imanari, Toshio et al., "High-performance liquid chromatographic analysis of glycosaminoglycan-derived oligosaccharides," *J. Chromatogr. A*, 720 (1996) 275-293.
Laremore, Tatiana N. et al., "Matrix-Assisted Laser Desorption/Ionization Mass Spectrometric Analysis of Uncomplexed Highly Sulfated Oligosaccharides Using Ionic Liquid Matrices," *Anal. Chem.* (Mar. 15, 2006) 78(6):1774-1779.
Rice, K.G. et al., "High-Performance Liquid Chromatographic Separation of Heparin-Derived Oligosaccharides," *Analytical Biochemistry* (1985) 150:325-331.

* cited by examiner

*Primary Examiner* — Maureen Wallenhorst
(74) *Attorney, Agent, or Firm* — Mintz, Levin, Cohn, Ferris, Glovsky and Popeo, P.C.

(57) ABSTRACT

The present invention describes an analytical method for detecting and quantitating poly-sulfated oligosaccharides, including Fondaparinux sodium, using hydrophilic interaction ultra-performance liquid chromatography (HILIC-UPLC) coupled with a charged aerosol detector (CAD) or a mass spectrometer (MS). This analytical method provides in-process control in a total synthesis of highly sulfated oligosaccharides by separation, quantification and mass identification. Systems and conditions utilizing such methods are also provided.

10 Claims, 13 Drawing Sheets

ANALYTICAL METHOD FOR DETECTING SULFATED OLIGOSACCHARIDES

CROSS-REFERENCES TO RELATED APPLICATIONS

Not Applicable

BACKGROUND OF THE INVENTION

Heparnoid (Heparin and Heparan sulfate) is a well-known regulatory mediator in numerous important biological processes. Heparnoid and its derivative, low-molecular weight heparin (LMWH), have been used as clinical anticoagulant drugs during surgery and kidney dialysis. For example, Fondaparinux sodium (CAS 114870-03-0) is a member of oligosaccharides/heparins with a chemical name of O-[2-Deoxy-6-O-sulfo-2-(sulfoamino)-alpha-D-glucopyranosyl]-(1-4)-O-(beta-D-glucopyranurosonyl)-(1-4)-O-[2-deoxy-3,6-di-O-sulfo-2-(sulfoamino)-alpha-D-glucopyranosyl]-(1-4)-O-(2-O-sulfo-alpha-L-idopyranurosonyl)-(1-4)-O-[2-deoxy-1-O-methyl-6-O-sulfo-2-(sulfoamino)-alpha-D-glucopyranoside] decasodium salt, and was developed by Choay, S. A. (see U.S. Pat. No. 4,818,816). The compound is a synthetic pentasaccharide Factor Xa inhibitor which is used as an anticoagulant drug for the prevention of deep vein thrombosis in patients who have had orthopedic surgery as well as for the treatment of deep vein thrombosis and pulmonary embolism. Fondaparinux sodium was approved by the United States Food and Drug Administration in 2001, marketed under the trade name Arixtra™. Fondaparinux sodium is administrated subcutaneously.

Analytical methods for heparin and heparan sulfate, traditionally involved reverse phase chromatographic and mass spectrometric (MS) techniques, but have limitations due to the high polarity, structural diversity, and sulfate lability of heparan sulfate. For instance, the quantitation of synthetic poly-sulfated oligosaccharides using MS is restricted because the ionization of poly-sulfated oligosaccharides tends to form various types of fragments and metal cation-coupled adducts with loss of sulfate groups. This leads to greater spectral complexity and signal splitting. In addition, it is difficult to demonstrate the degree of loss of sulfate groups during the analysis because it depends on the concentration and charge state of sulfated oligosaccharides. Improved analytical methods for poly-sulfated oligosaccharides have been the target of a number of research groups.

Catalin et al. (Anal. Chem. 2009, 81, 3485) and Tatiana et al. (Anal. Chem. 2006, 78, 1774) have each described the characterization of poly-sulfated oligosaccharides by using electrospray ionization mass spectrometry (ESI-MS) and matrix-assisted laser desorption and ionization mass spectrometry (MALDI-MS). However, the current methods using the coupling of liquid chromatograph (LC) with mass spectrometry does not provide on-line in-process resolution/separation of peaks and hence the identification of the structure related impurities and/or quantitation of the poly-sulfated oligosaccharides cannot be established during the production of synthetic poly-sulfated oligosaccharides.

Imanari et al. (J. Chromatogr., A 1996,720, 275.) and Rice et al. (J. Anal. Biochem. 1985, 150, 325.) illustrated the analytical method of poly-sulfated oligosaccharides by strong anion exchange chromatography (SAX). This method appears to separate highly sulfated oligosaccharides via the difference in charge density, but it remains difficult to directly couple SAX with a detection method like MS due to the use of nonvolatile salt in the mobile phase composition.

Still other problems associated with analytical methods for poly-sulfated oligosaccharides are due to the non-chromophore characteristics (very low UV absorption) of poly-sulfated oligosaccharides, which can restrict the use of traditional UV detectors. The other universal detectors such as refractive index (RI) and evaporative light scattering (ELSD) also lack enough detecting sensitivity for poly-sulfate oligosaccharides.

Although some methods of detection of poly-sulfated oligosaccharides have been disclosed, a number of limitations remain. Thus, there is a continuing need for improved methods for the separation, quantitation and mass identification of poly-sulfated oligosaccharides. The stable, sensitive and in-process control (IPC) methods disclosed herein address this need and other needs.

BRIEF SUMMARY OF THE INVENTION

Provided herein is a method for detecting poly-sulfated oilgosaccharides, using a hydrophilic interaction ultra-performance liquid chromatography (HILIC-UPLC) coupled with a charged aerosol detector (CAD) or a mass spectrometer (MS). The methods provided herein allow for improved peak resolution thereby allowing for subsequent quantitation of poly-sulfated oligosaccharides and/or impurities in the sample.

The use of HILIC overcomes the challenge of retaining and separating extremely polar oligosaccharides. The retention mechanism for HILIC is very intricate and is a multi-modal combination of liquid-liquid partitioning, adsorption, ionic interaction and hydrophobic interaction. Therefore, HILIC, in comparison to reverse phase liquid chromatography (RPLC), provides unique selectivity and retention characteristics.

As provided herein, the stationary phase used in HILIC column is, in one group of embodiments, an amide-bonded stationary phase.

In another embodiment, the mobile phase used in HILIC column comprises a salt. In one group of embodiments, the salt is ammonium formate. The use of ammonium formate, in comparison to pyridinium formate and ammonium acetate, provides better performance for retention, selectivity and low noise level baseline.

In some embodiments, the concentration of the salt is higher than 50 mM. In some selected embodiments, the concentration is higher than 100 mM. Typically, the molar strength of the salt additive in the mobile phase composition can have a significant impact on chromatographic retention, selectivity and sensitivity. As the molarity of the salt additive increases, the ionic strength of the mobile phase and the solute is overpowered by the liquid-liquid partitioning interaction which dominates the retention mechanism rather than the ion exchange effect. However, it has now been discovered that in the case of acidic analytes, such as poly-sulfated oligosaccharides, retention is enhanced as the molarity of the salt additive increases. In particular, the resolution of peaks is further improved as the salt concentration is increased from 50 mM to about 200 mM.

In one group of embodiments, the solvent of the mobile phase used in the HILIC column is acetonitrile.

In some embodiments, the detector used for the quantitation of poly-sulfated oligosaccharides is a charged aerosol detector (CAD). During the analysis using CAD, aerosol particles are charged with an ionized gas (typically nitrogen). After the removal of high-mobility particles (mainly excess $N_2$ ions), the aerosol particles are then electrically measured. Most importantly, the method has been demonstrated to provide a uniform response for nonvolatile analytes independent of their nature. Thus, the combination of (1) a separation technique utilizing HILIC, or HILIC-UPLC, and (2) a detection technique such as MS or CAD allows for detection, identification and/or quantification of poly-sulfated thereby providing an effective way for analysis of synthetic poly-sulfated oligosaccharides.

In accordance with one selected embodiment of the present invention, the poly-sulfated oilgosaccharide detected and/or quantitated by the methods described herein is Fondaparinux sodium.

DETAILED DESCRIPTION OF THE INVENTION

I. General

Figure 1A:
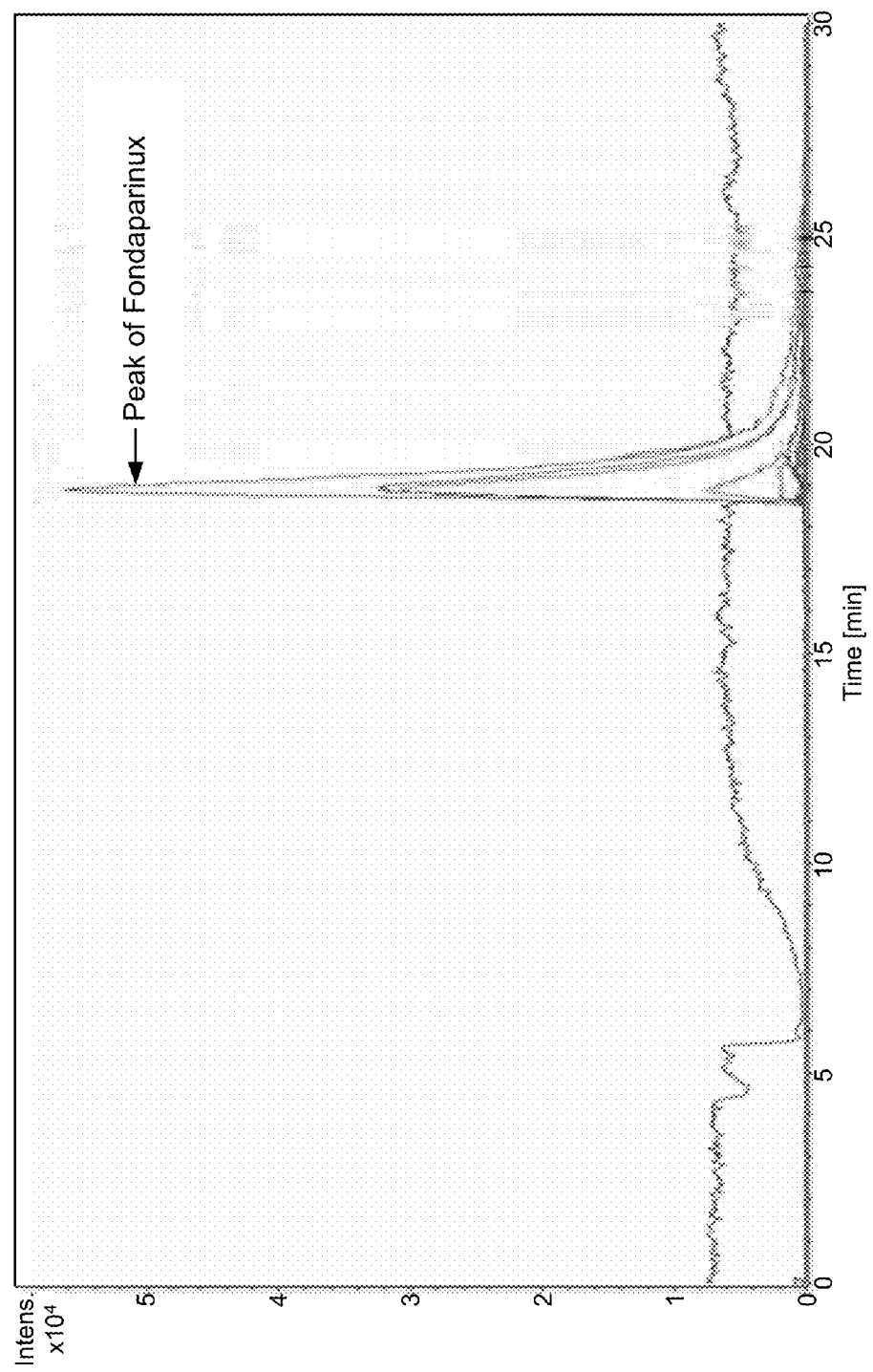
FIG. 1(a) provides the chromatograms of HILIC-CAD for Fondaparinux Sodium using Merck, Sequant Zic®-Hilic (3.5 um 2.1×250 mm).
Figure 1B:
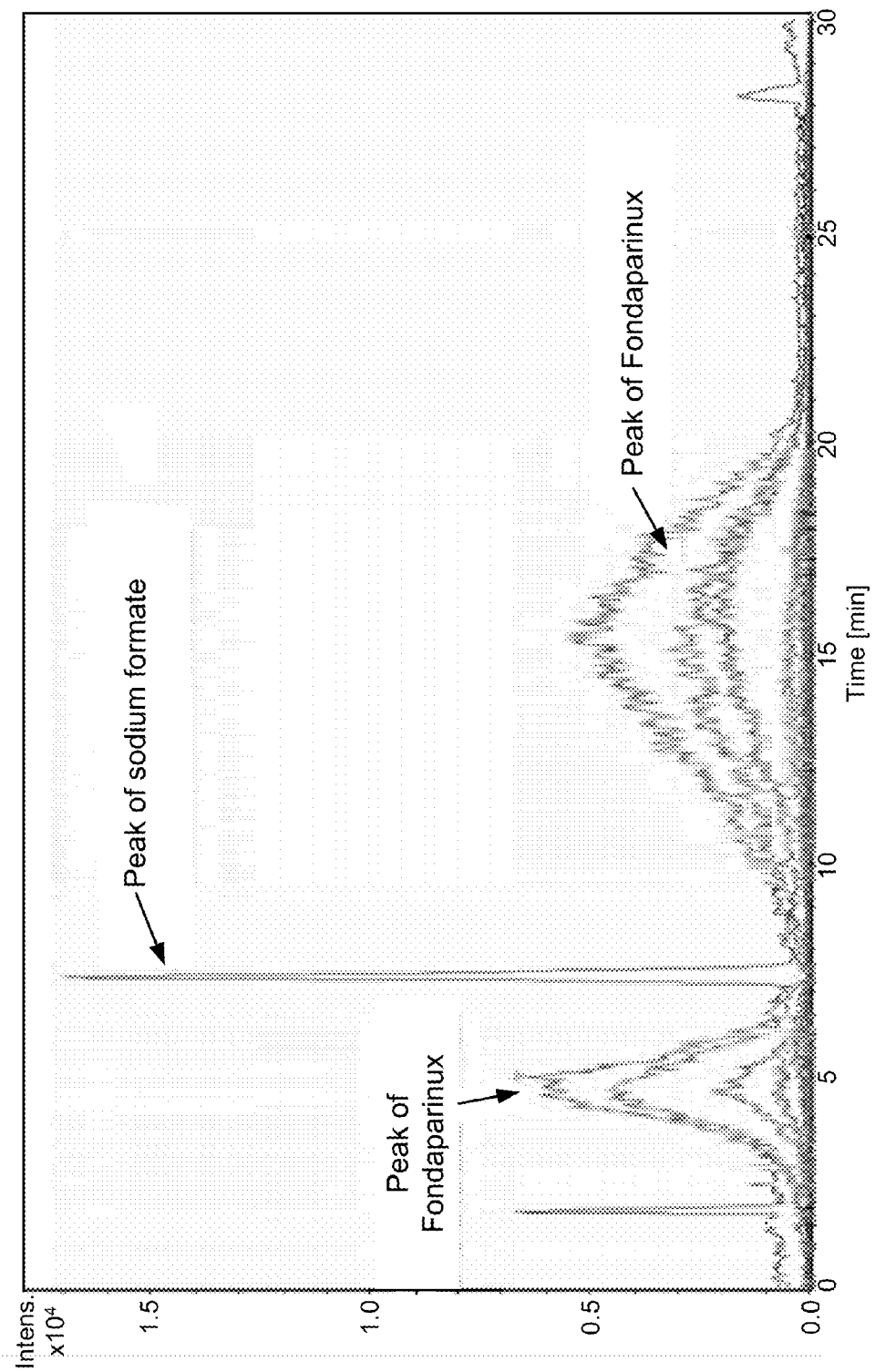
FIG. 1(b) provides the chromatograms of HILIC-CAD for Fondaparinux Sodium using Merck, Sequant Zic®-pHilic (5 um 4.6×150 mm).
Figure 1C:
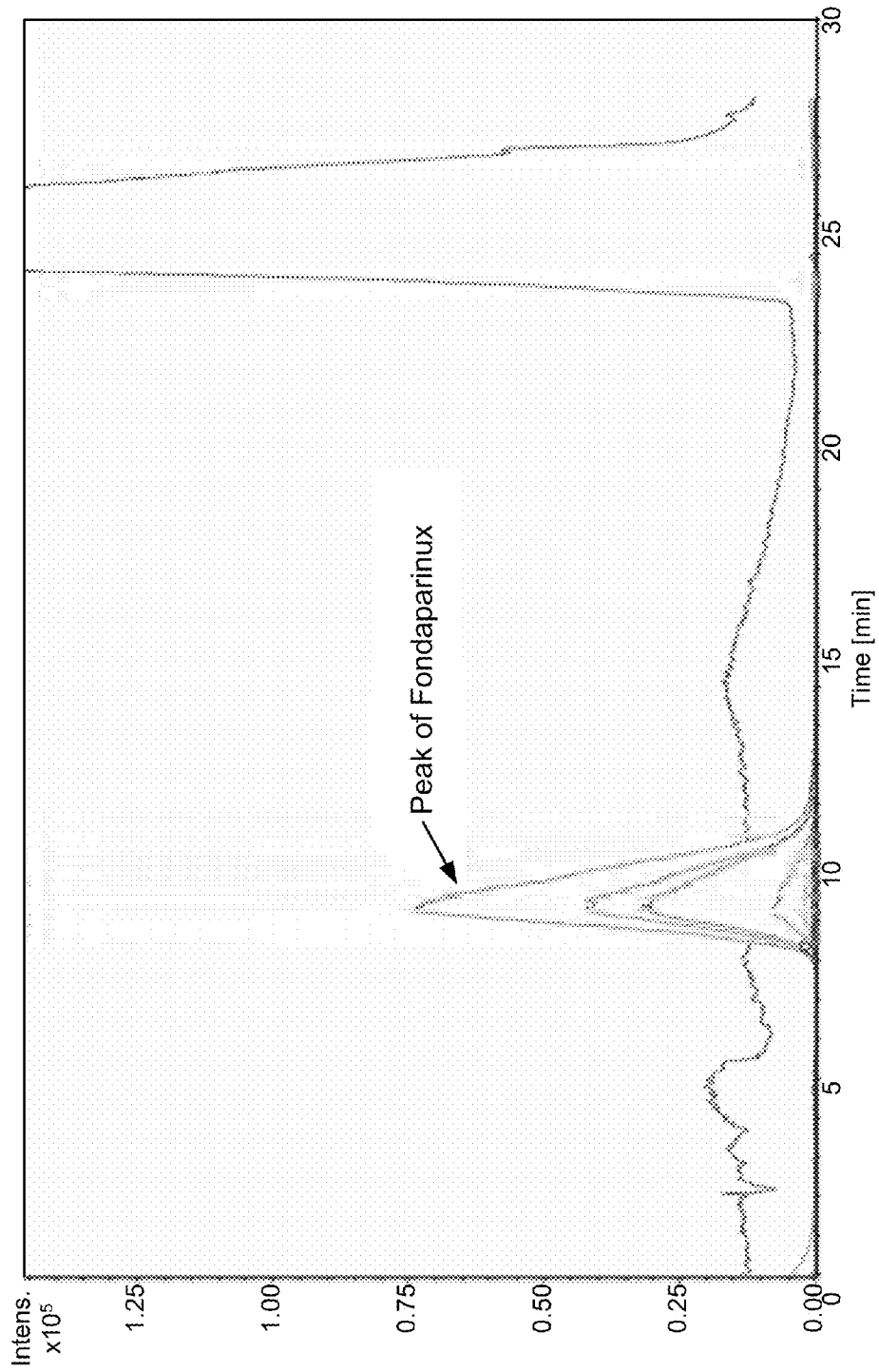
FIG. 1(c) provides the chromatograms of HILIC-CAD for Fondaparinux Sodium using Phenomenex, Synergi Polar-RP (4 um 4.6×250 mm).
Figure 1D:
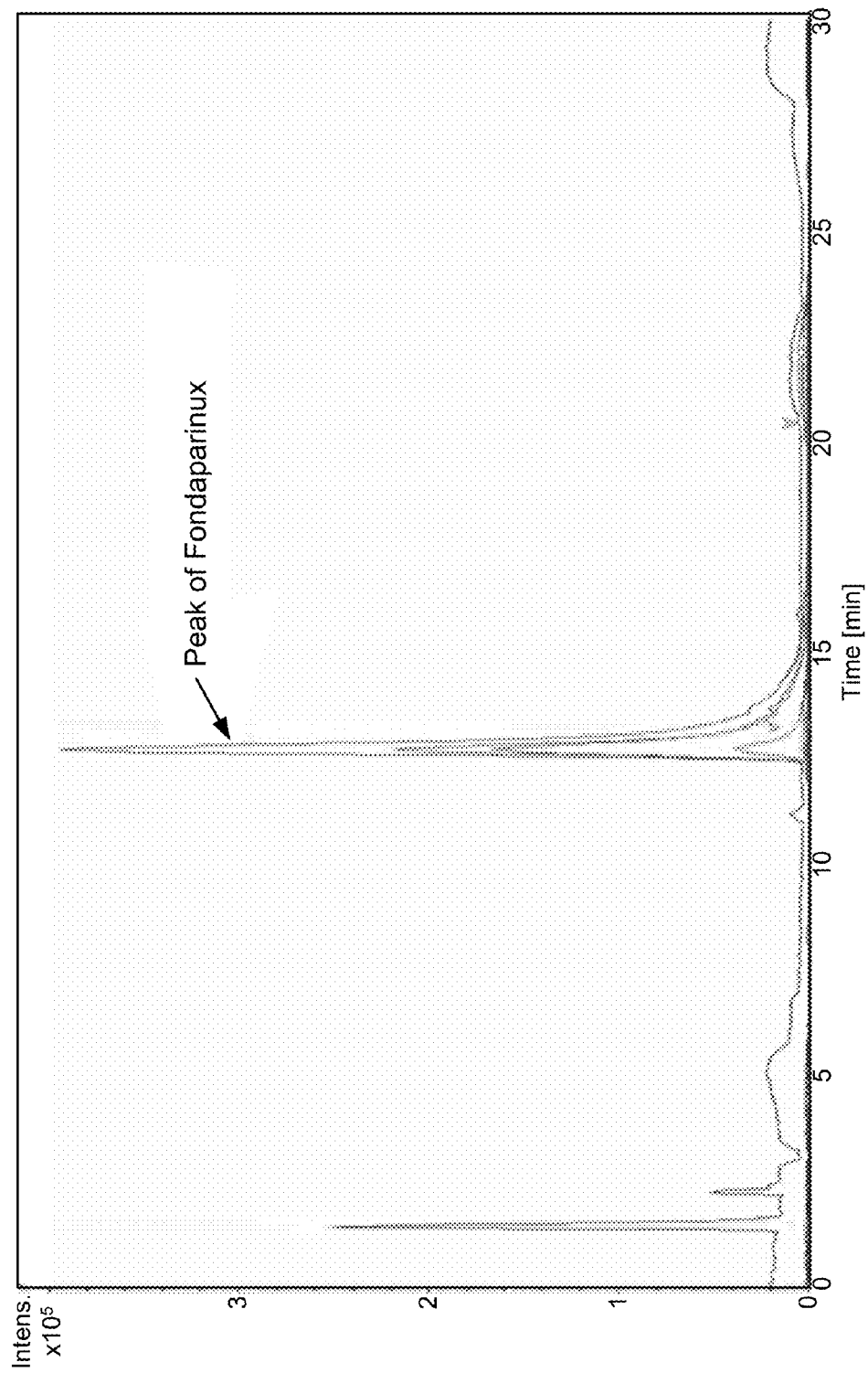
FIG. 1(d) provides the chromatograms of HILIC-CAD for Fondaparinux Sodium using Phenomenex, Synergi Fusion-RP (4 um 4.6×150 mm).
Figure 1E:
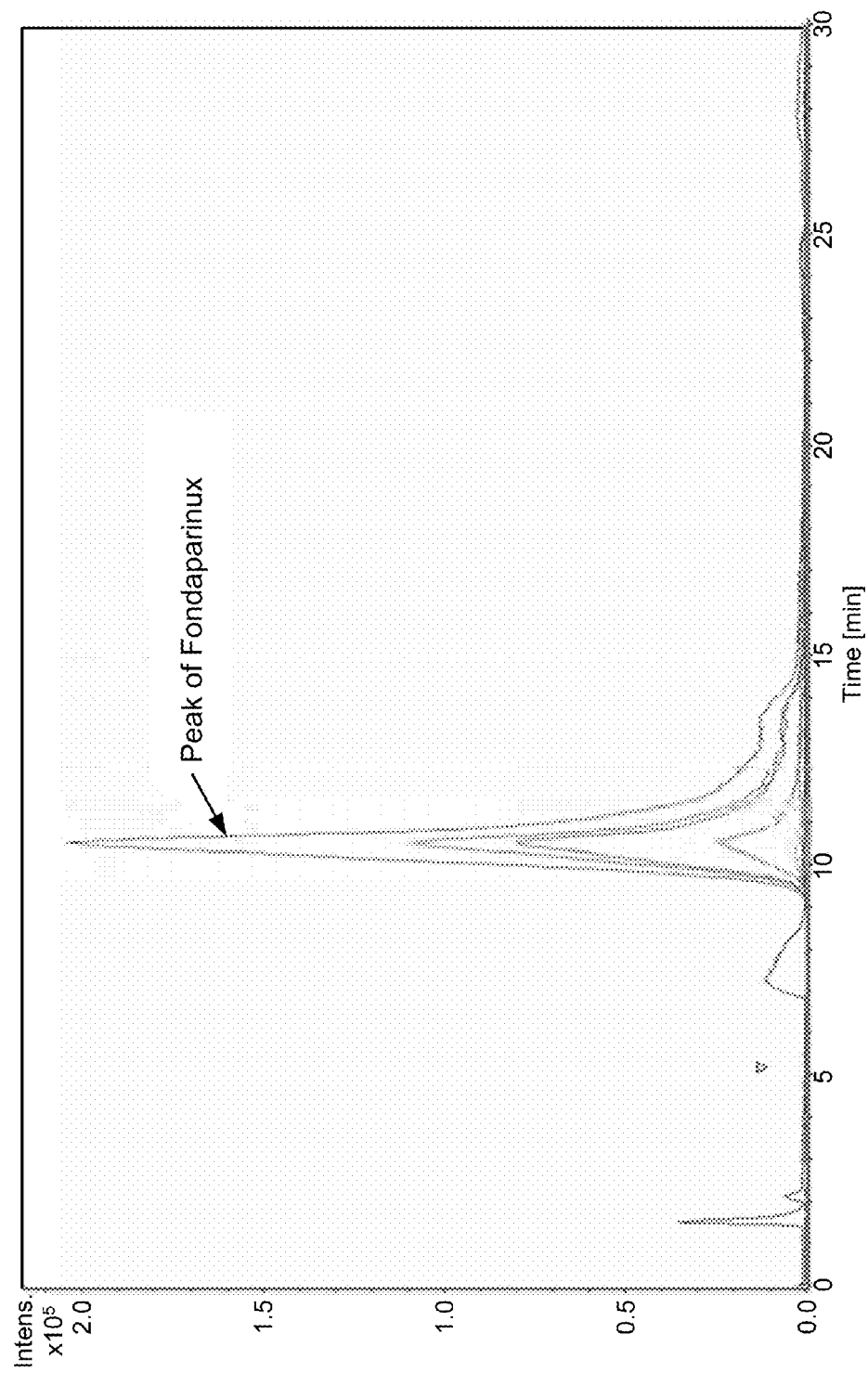
FIG. 1(e) provide the chromatograms of HILIC-CAD for Fondaparinux Sodium using Sepax Polar-Pyridine (1.8 um 2.1×150 mm).
Figure 1F:
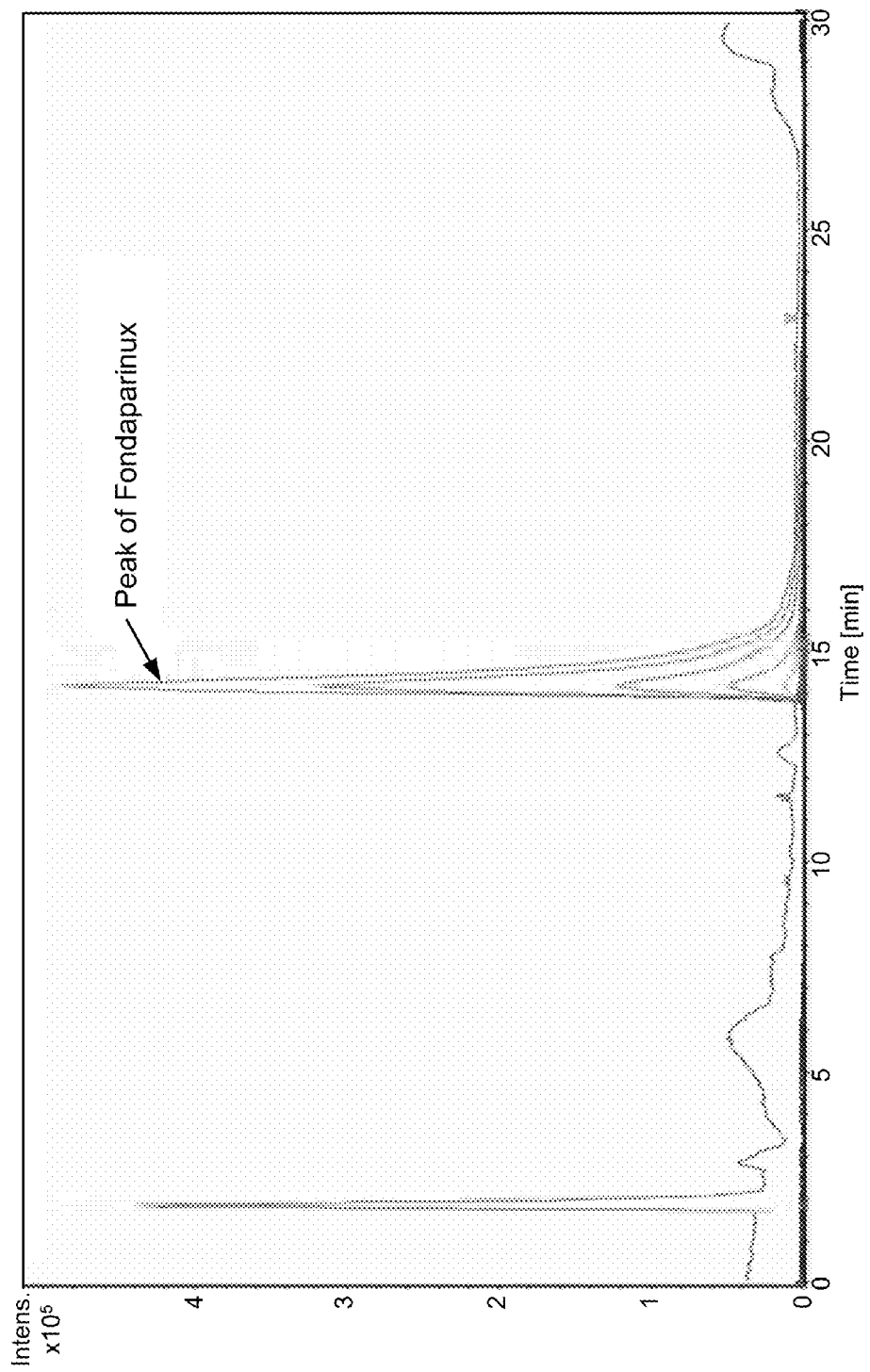
FIG. 1(f) provides the chromatograms of HILIC-CAD for Fondaparinux Sodium using ES, Epic Diol (1.7 um 2.1×150 mm).
Figure 1G:
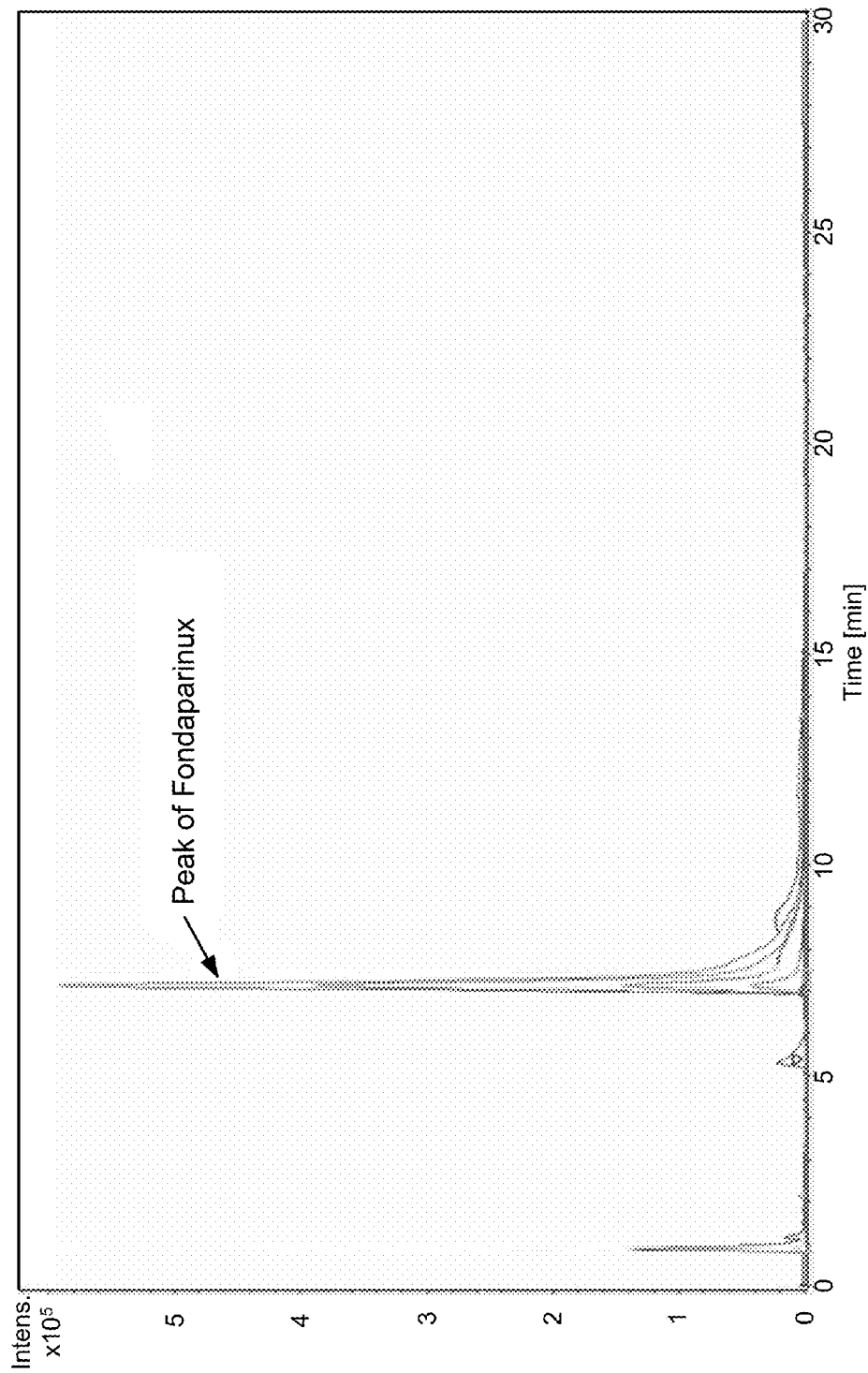
FIG. 1(g) provides the chromatograms of HILIC-CAD for Fondaparinux Sodium using Waters, Acquity BEH HILIC (1.7 um 2.1×150 mm).
Figure 1H:
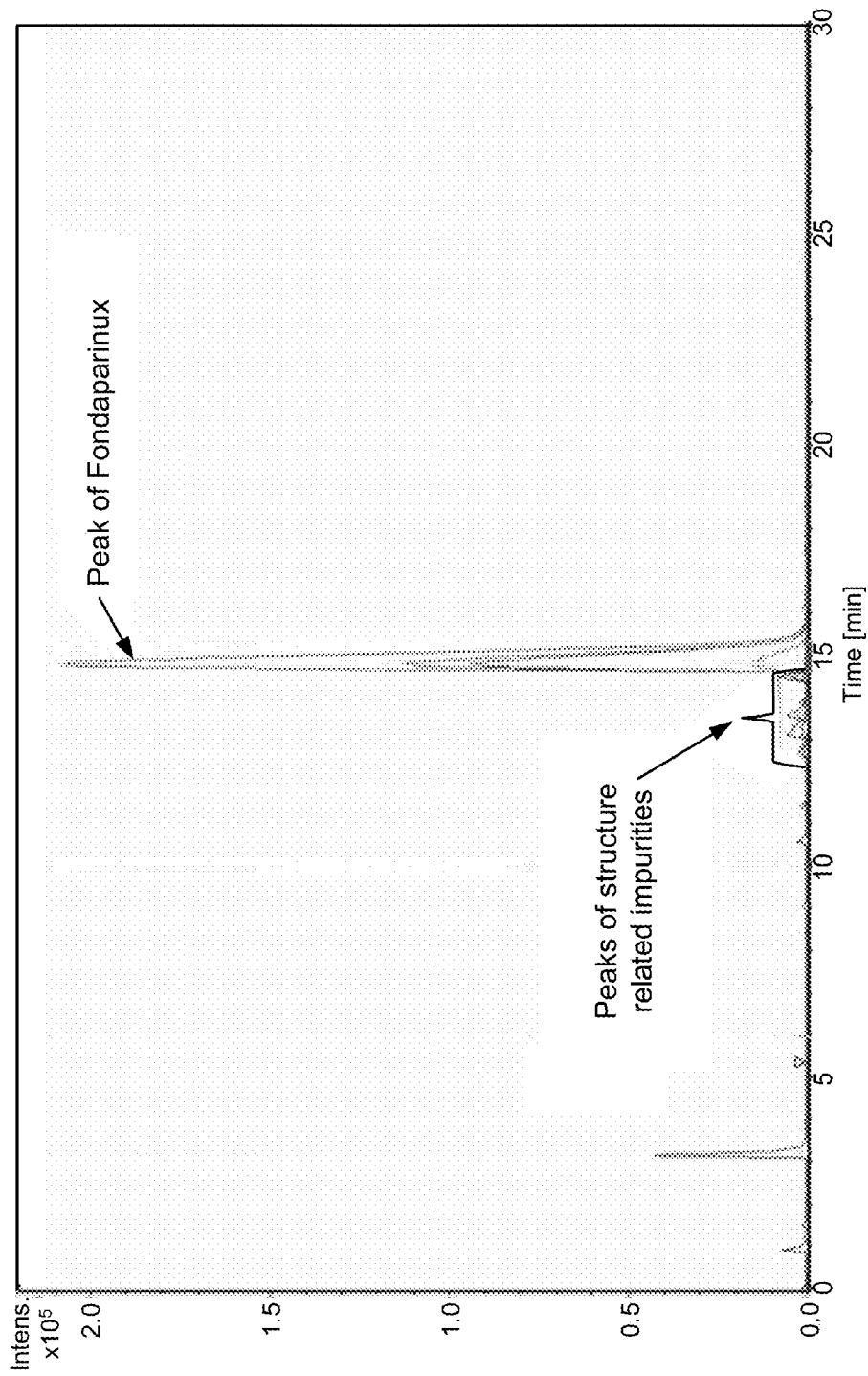
FIG. 1(h) provides the chromatograms of HILIC-CAD for Fondaparinux Sodium using Waters, Acquity BEH Amide (1.7 um 2.1×150 mm).

Provided herein is a straightforward in-process analytical method developed for poly-sulfated oligosaccharides involving the application of HILIC-UPLC, CAD and MS for separation, quantification and mass identification, respectively. The in-process control (IPC) during manufacturing is a key for ensuring quality control in a total synthesis of highly sulfated oligosaccharides. The analytical methods described herein are usable as IPC methods. Advantageously, the analytical methods described herein are stable, easy to use, sensitive, and ensure the production of a quality chemical entity within the expected yields.

II. Embodiments of the Invention

In view of the above, provided herein is method for detecting and quantitating one or more poly-sulfated oligosaccharides in a sample, the method comprising:
(a) subjecting said sample to chromatography on a hydrophilic interaction ultra-performance liquid chromatography (HILIC-UPLC) column coupled with a charged aerosol detector (CAD) or a mass spectrometer (MS), wherein the stationary phase used in HILIC column is an amide-bonded stationary phase; and
(b) determining the amount of poly-sulfated oligosaccharides in the sample.

The samples used in the present methods are typically the output of synthetic production methods of poly-sulfated oligosaccharides. As a result, samples of the final step in the synthetic procedures can be analyzed according to the present methods by selecting aliquots of reaction mixtures. The sampling of reaction mixtures allows for detection and/or identification and/or quantitation of impurities and/or poly-sulfated oligosaccharides. The sampling of reaction mixture also allows for determination of the extent of completion of a reaction. Alternatively, the final product can be subjected to the present methods to determine if further purification is needed.

The conditions for chromatography using hydrophilic interaction ultra-performance liquid chromatography will generally involve those conditions known to one of skill in the art, including, but not limited to column selection (size, length and stationary phase) as well as the mobile phase and/or pH of the mobile phase.

Selection of a column will generally involve selection from commercially prepared column such as those available from Waters, ThermoFisher, Merck, Phenomenex, Shodex, Nucleosil, and Sepax. In one group of embodiments, the column has a stationary phase of neutral charge (e.g., diol phase or amide phase), a charged stationary phase (e.g., silica phase, aminopropyl phase), or a zwitterionic stationary phase. In one selected group of embodiments, the stationary phase is an amide-bonded stationary phase. Examples 1-10 illustrate the results obtained from the use of various stationary phases using the methods described herein.

One of skill in the art will appreciate that flow rates will also affect the separation and resolution obtained.

The solvent used in the mobile phase is generally a polar, aprotic organic solvent or a mixture of polar, aprotic organic solvents. In one group of embodiments, the solvent of the mobile phase used in HILIC column is acetonitrile, acetone or a mixture of acetonitrile and acetone. Examples 13a-13d illustrate the effect of various solvents and/or mixtures of solvents in the detection and/or quantitation of poly-sulfated oligosaccharides using the methods described herein.

In other embodiments, the mobile phase will also comprise a salt, generally a salt selected from ammonium formate, pyridinium formate and ammonium acetate, and mixtures thereof. In certain selected embodiments, the mobile phase will comprise ammonium formate. In an additional group of embodiments, the mobile phase comprises a salt selected from ammonium citrate and/or ammonium oxalate. Examples 11a-11d illustrate the effect of various salts in the mobile phase in the detection and/or quantitation of poly-sulfated oligosaccharides using the methods described herein.

The concentration of the salt used in the mobile phase will generally be from 25 to about 400 mM, though some optimal results are found when the salt is present in the mobile phase at concentrations of from 50 to about 200 mM. In some embodiments, the salt is present in the mobile phase at concentrations of about 50-100 mM, from about 100-200 mM, and from about 75 to 175 mM. Examples 12a-12d illustrate the effect of various salt concentrations on peak resolution and peak width during the detection and/or quantitation of poly-sulfated oligosaccharides, when using the methods described herein, by employing ammonium formate as the salt.

In specific embodiments, the methods described above are useful for detection and/or quantitation of the poly-sulfated oligosaccharide fondaparinux having the structure:

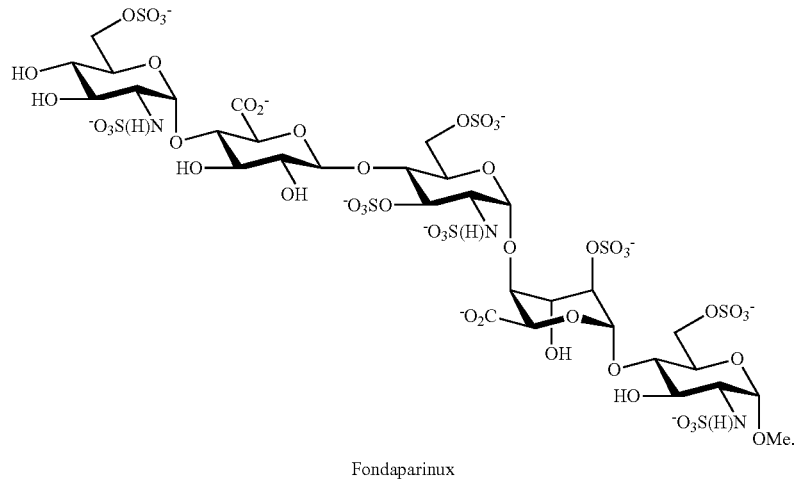

Fondaparinux

In another aspect, provided herein is a method for detecting and quantitating fondaparinux in a sample, the method comprising:

(a) subjecting said sample to chromatography on a hydrophilic interaction ultra-performance liquid chromatography (HILIC-UPLC) column coupled with a charged aerosol detector (CAD) or a mass spectrometer (MS), wherein the stationary phase used in HILIC column is an amide-bonded stationary phase, the mobile phase used in said chromatography is acetonitrile, and the mobile phase comprises ammonium formate in a concentration of from about 100 mM to about 200 mM; and (b) determining the amount of fondaparinux in the sample As used above and herein, "determination" of the amount of fondaparinux in the sample, or "quantitation of fondaparinux" is effected in one or more ways which are readily available to one of skill in the art. Generally, instruments for UPLC-MS—and/or CAD are sold with pre-installed programs and/or algorithms which can calculate the relative amounts of substances in a sample (e.g., by calculating the areas under the peaks and/or measuring relative intensities of peaks). According to the response of the instrument and the concentrations of a series of external standards, an external calibration curve can be obtained by using the conventional regression analysis. The sample concentration can then be determined by the external calibration curve. As used above and herein, "detection" (e.g., of fondaparinux and/or impurities) in a sample comprises, in an exemplary embodiment, the recording of chromatograms using the methods described herein (e.g., by use of HILIC-UPLC) and peak identification using a coupled techinque such as CAD or MS thereby confirming (detecting) the presence or absence of fondaparinux and/or impurities in the sample.

III. Examples

The following examples are presented to describe the invention in further detail. However, the present invention is by no means restricted to the specific embodiments described herein.

Instrument

The instruments involved in UPLC-MS study are Ultimate 3000 (UPLC) and micrOTOF-Q II™ (MS) which were manufactured by Thermo Fisher Dionex and Bruker Daltonics, respectively. The instruments involved in UPLC-CAD are ACQUITY UPLC® System and Thermo Scientific Dionex Ultra CAD which were manufactured by Waters Corporation and Thermo Fisher Dionex, respectively.

Parameters

The conditions for analysis are set forth below.

1. An Amide-HILIC type column is used as the analytical column for analyzing poly-sulfonated oligosaccharides.

2. The concentration of ammonium formate used in the mobile phase is 100 mM or higher than 100 mM.

3. The volume proportion of ammonium formate:acetonitrile in the mobile phase composition is in the range of 95%-5% :5-95%.

4. The range of flow rate used in the examples below is 0.4 mL/min-1 mL/min

5. The range of column temperatures used in the methods described herein is 10° C.-70° C.

6. The range of nebulization temperature of charged aerosol detector used in this method is 10° C.-30° C.

7. The concentration of testing sample is from 15 μg/mL to 30 mg/mL.

8. The injection volume of testing sample is from 1 μ to 5 μL.

Sample Preparation

The sample is dissolved in a mixture of water and acetonnitrile (1:1; 30 mg/mL).

Examples 1-10

Comparison of Different Types of HILIC Columns and General LC Conditions

The sample prepared as above is analyzed by different types of HILIC columns as shown in Table 1. The chromatograms recorded using various columns are shown in FIGS. 1(a)~(h) and peak identification of Fondaparinux was confirmed by LC-MS.

TABLE 1

| | Type | Brand |
|---|---|---|
| 1 | BEH-HILIC (—OH) | Waters |
| 2 | BEH-Amide | Waters |

TABLE 1-continued

| | Type | Brand |
|---|---|---|
| 3 | Accucore | Thermo |
| 4 | Zic-Hilic | Merck |
| 5 | Polar-RP | Phenomenex |
| 6 | Fusion-RP | Phenomenex |
| 7 | NH2P-50 | Shodex |
| 8 | 5-NH2 | Nucleosil |
| 9 | Polar-Pyridine | Sepax |
| 10 | Polar-Imidazole | Sepax |

Figure 2A:
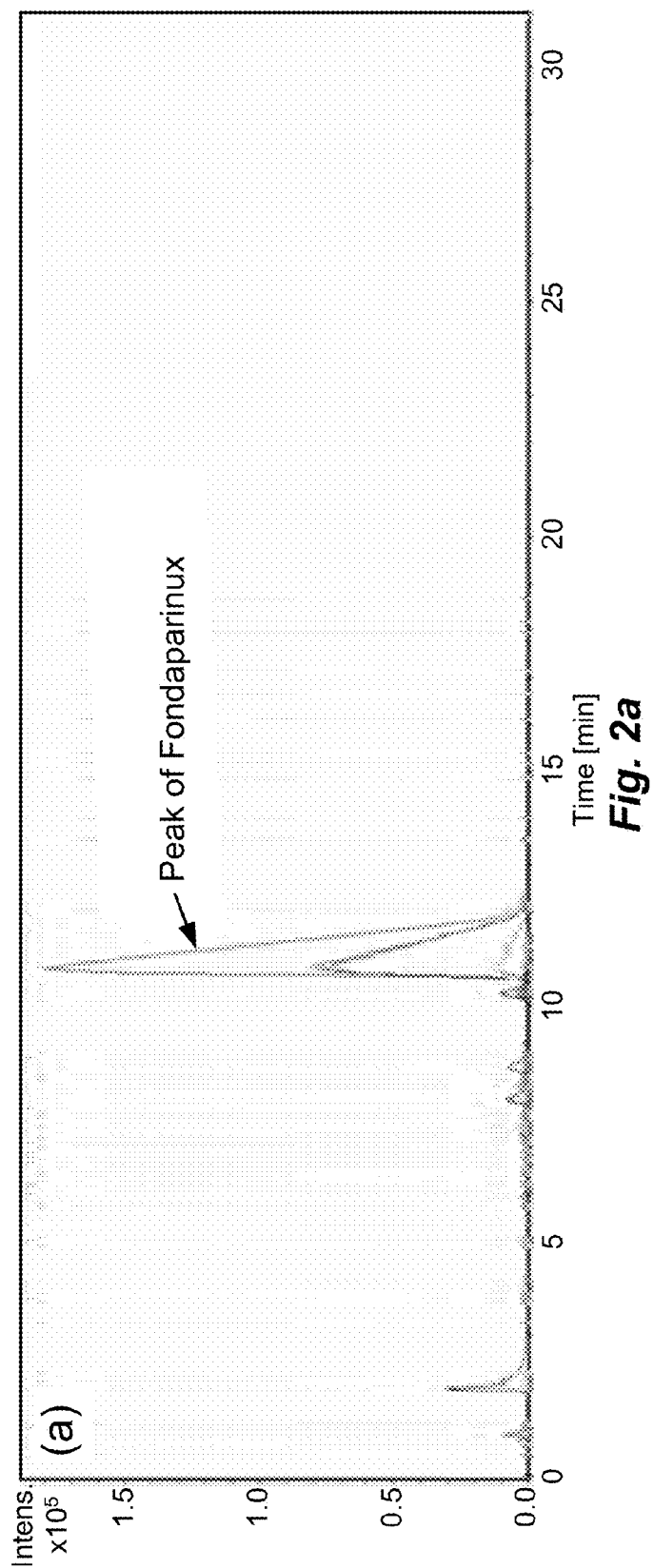
FIG. 2 provides the chromatogram for Fondaparinux Sodium using Waters, BEH Amide column (a) full scale and (b) expanded scale.
Figure 2B:
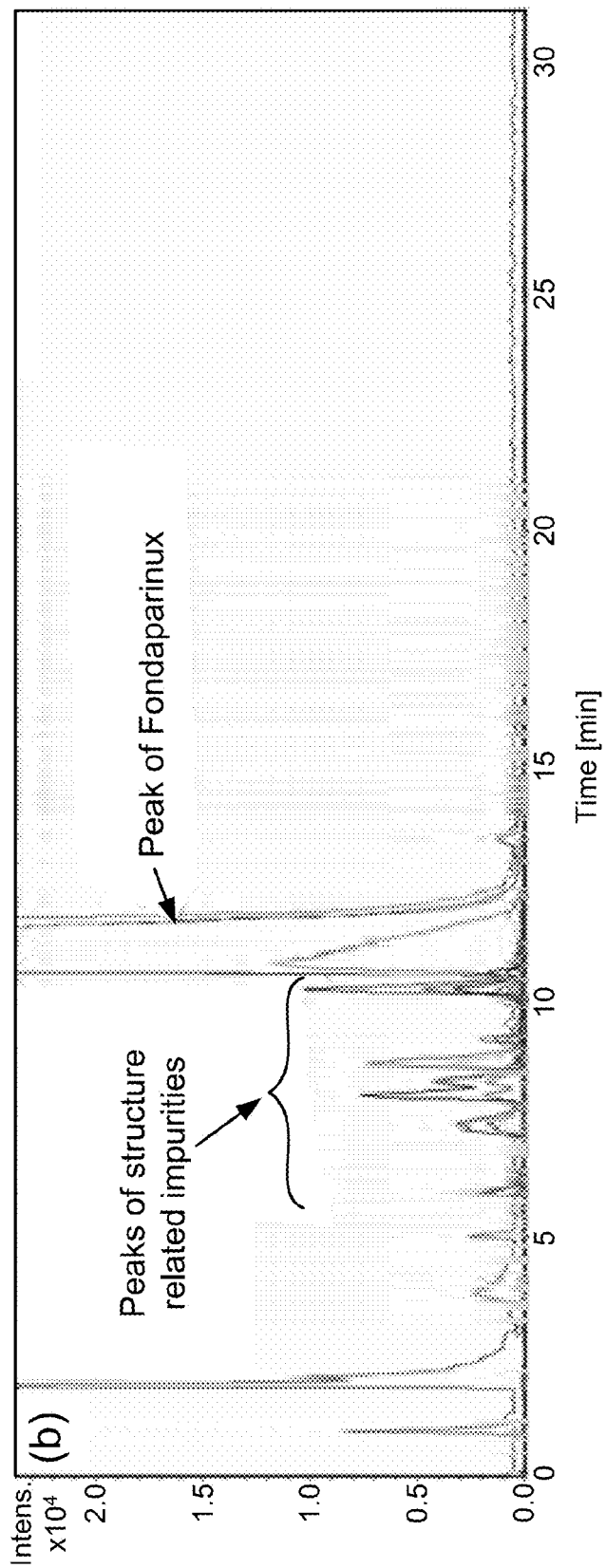

In majority of Examples 1-10, the peak of Fondaparinux was found to be asymmetric with a poor separation from the impurities with one exception, the case of Waters BEH Amide column. The LC conditions for Waters BEH Amide were optimized and a typical chromatogram is shown in FIG. 2. This study demonstrates that the amide type of HILIC column provides a relatively better choice for the analysis of this synthetic poly-sulfated pentasaccharides among various types of HILIC columns.

Examples 11a~11d

Effect of Various Salts

Figure 3:
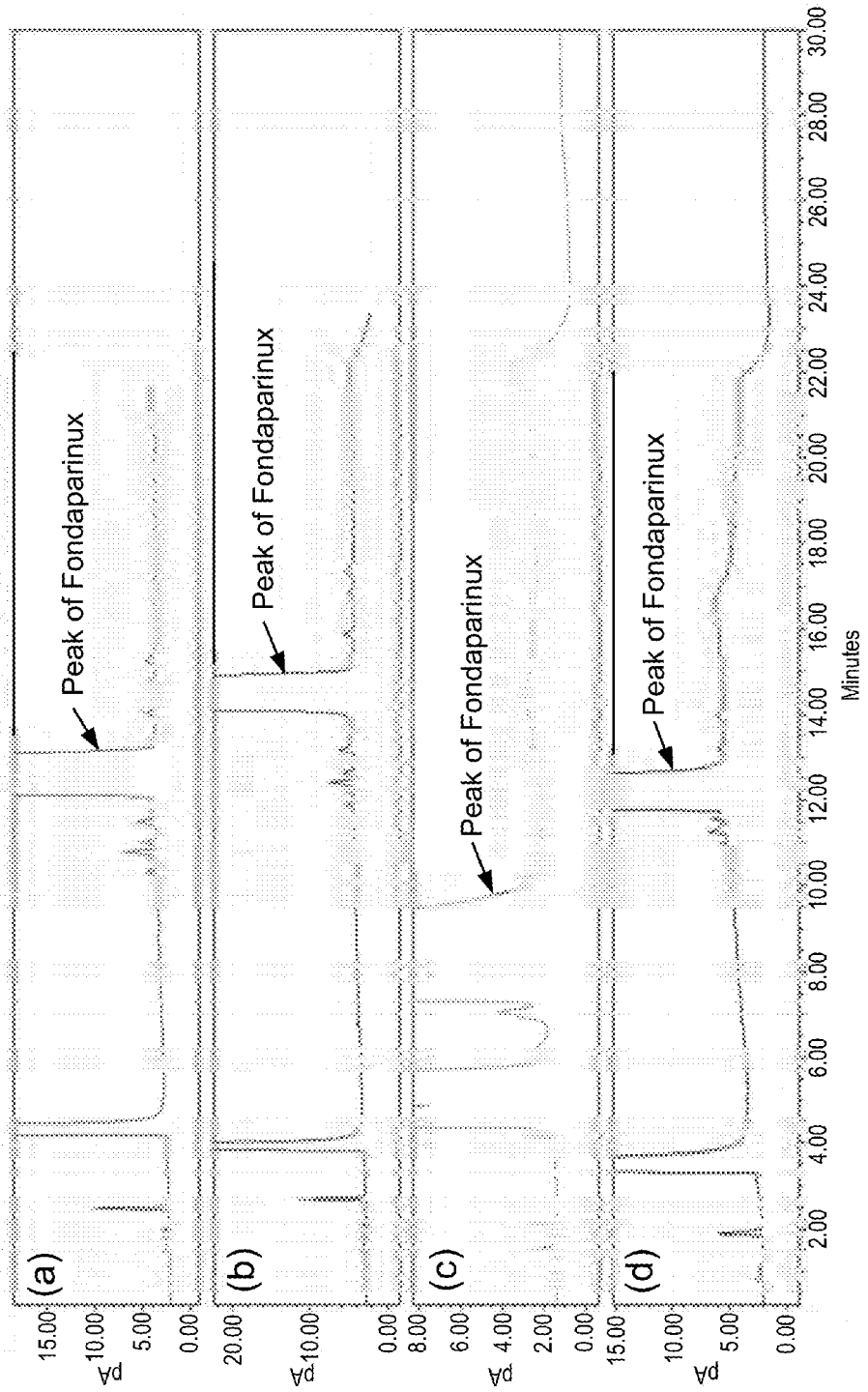
FIG. 3 provides the chromatograms in expanded scale of the drug substance analyzed using different types of salt (a) 50 mM ammonium formate (b) 100 mM ammonium formate (c) 100 mM pyridinium formate and (d) 50 mM ammonium acetate FIG. 4 provides the chromatograms in expanded scale of the drug substance analyzed using various concentrations of ammonium formate (in expanded scale) (a) 50 mM (b) 100 mM (c) 125 mM (d) 150 mM (e) 175 mM and (f) 200 mM.

Three different salts, ammonium formate, pyridinium formate and ammonium acetate were compared. The analysis condition is shown in Table 2. The results are shown in FIG. 3.

TABLE 2

| | Example | | | |
|---|---|---|---|---|
| | 11a | 11b | 11c | 11d |
| Salt | 50 mM ammonium formate | 100 mM ammonium formate | 100 mM pyridinium formate | 50 mM ammonium acetate |

The best chromatographic performance in terms of retention, selectivity and a low noise level baseline was the mobile phase containing ammonium formate salt, at both 50 mM and 100 mM concentration levels (FIGS. 3a and 3b, respectively). Pyridinium formate (FIG. 3c) and ammonium acetate (FIG. 3d) showed higher baseline noise and less retention for the analyte of interest. Based on the study, ammonium formate was chosen to be the salt additive in the mobile phase composition.

Examples 12a~12f

Effect of Salt Concentrations

Figure 4:
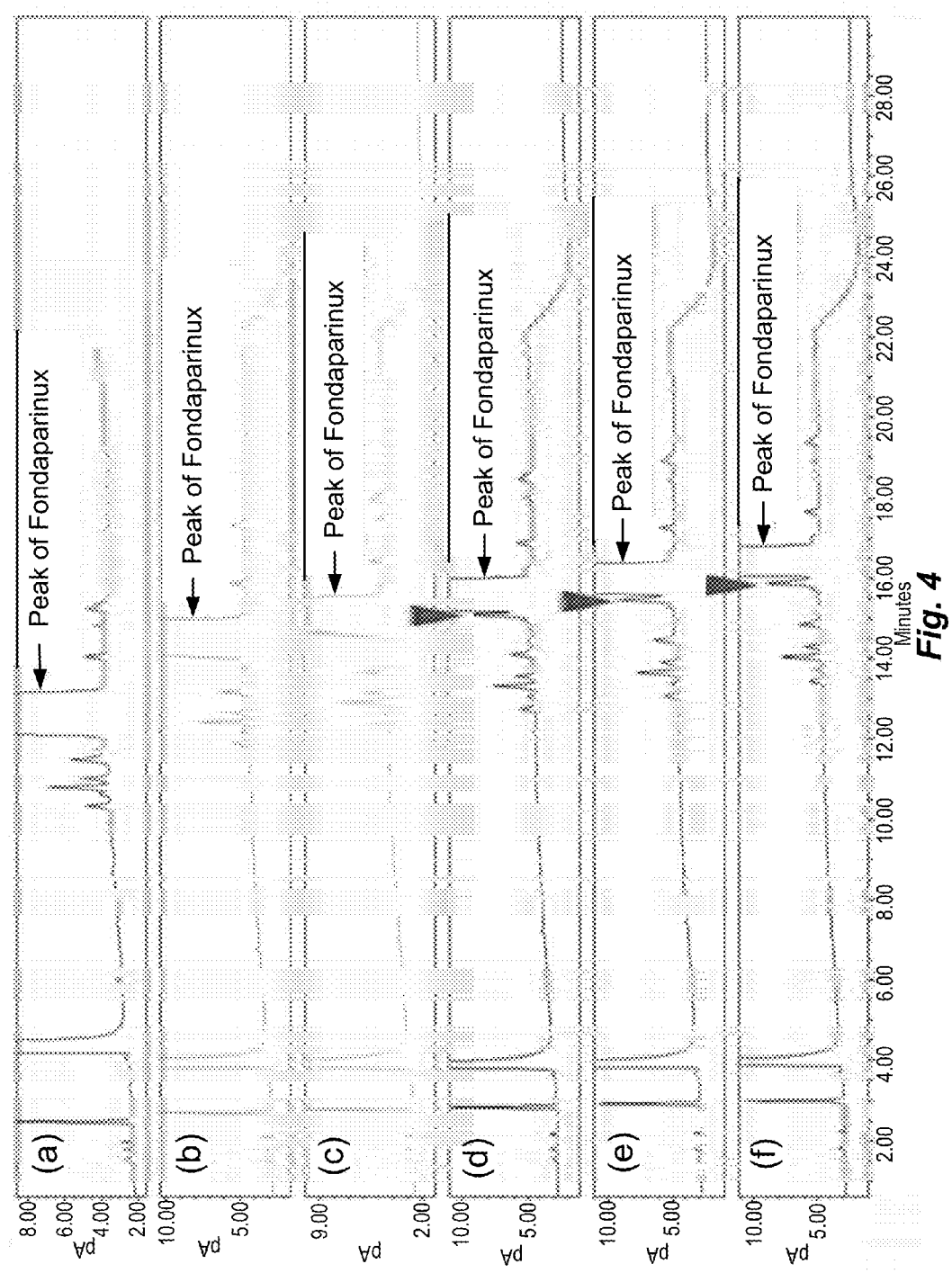

Mobile phase compositions containing various concentrations of ammonium formate salt were studied to optimize the LC conditions. The concentrations of ammonium formate for Examples 12a~12f are provided in Table 3. The representative chromatograms are shown in FIG. 4.

TABLE 3

| Example | 12a | 12b | 12c | 12d | 12e | 12f |
|---|---|---|---|---|---|---|
| concentrations of ammonium formate | 50 mM | 100 mM | 125 mM | 150 mM | 175 mM | 200 mM |

The impurity profile was found to be very similar for chromatograms obtained with 50 mM and 100 mM salt concentrations (FIGS. 4a and 4b). As the salt concentration increased, a small peak (marked with a dark triangle, see FIGS. 4d, 4e and 4f), right before the main peak, Fondaparinux, was observed. The resolution of this new peak from the main peak was further improved as the salt concentration increased from 150 mM to 200 mM of ammonium formate. In addition, it was clear that the bandwidth of the main peak narrowed as the salt concentration increased to 175 mM; no further improvement on resolution and peak shape was observed when the salt concentration was increased beyond 175 mM.

Examples 13a-13b

Effect of Solvent

Figure 5:
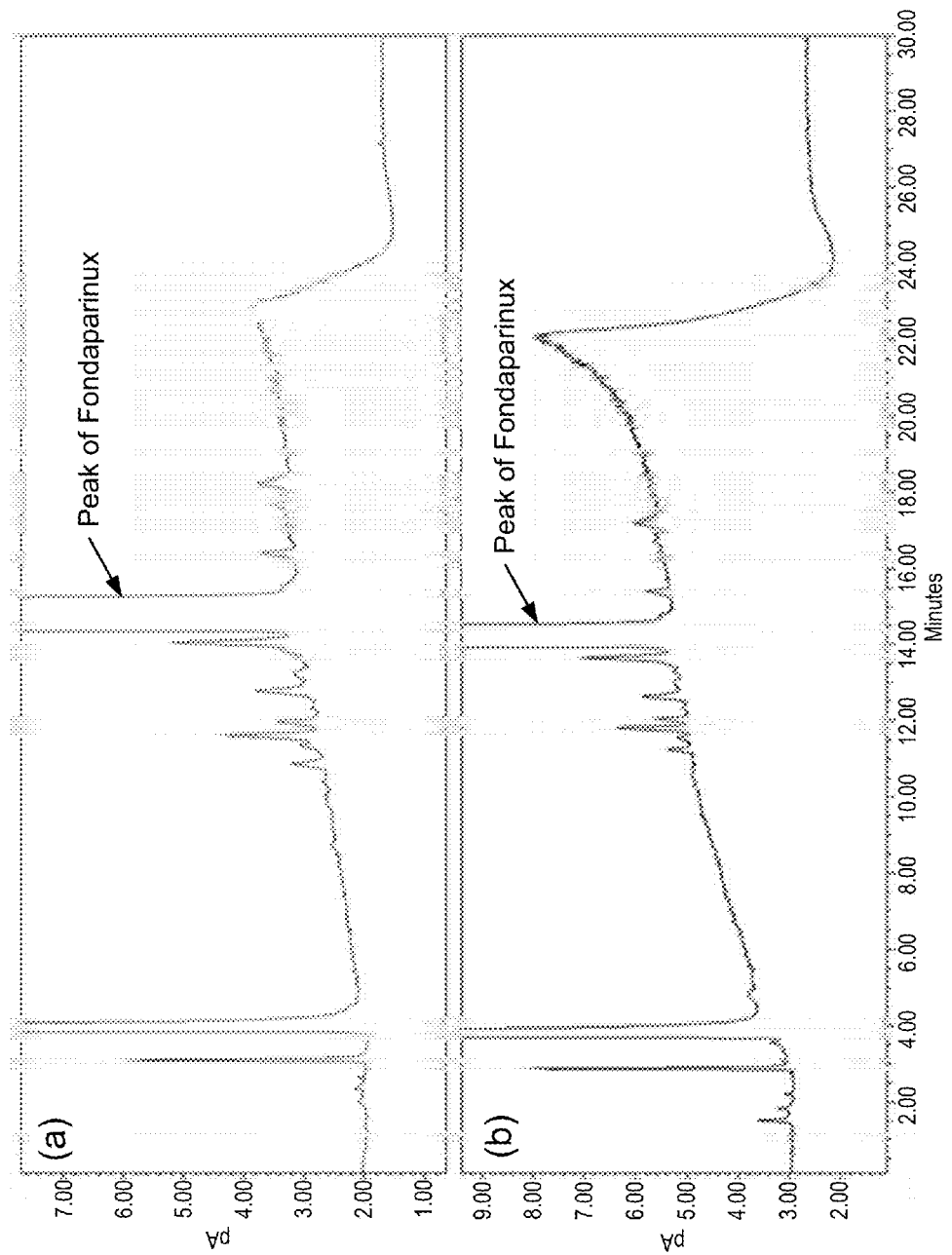
FIG. 5 provides the chromatograms in expanded scale of the drug substance analyzed using different organic solvents to be mobile phase (a) mobile phase A: 200 mM ammonium formate; mobile phase B: acetone and acetonitrile, 1/1 (b) mobile phase A: 200 mM ammonium formate; mobile phase B: acetonitrile.

Examples 13a and 13b use the mixtures of acetonitrile and acetone and acetonitrile respectively as the solvent of the mobile phase for analyzing Fondaparinux Sodium according to the present invention. Although the results shown in FIG. 5 indicate no obvious difference in selectivity between acetonitrile system and mixture (acetonitrile and acetone) system, a higher back pressure was observed in the system comprising the acetone/acetonitrile mixture than in the acetonitrile system.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for detecting and quantitating one or more poly-sulfated oligosaccharides in a sample, the method comprising:
   (a) subjecting said sample comprising said one or more poly-sulfated oligosaccharides to chromatography on a hydrophilic interaction ultra-performance liquid chromatography (HILIC-UPLC) column having an amide-bonded stationary phase and a mobile phase, to separate said one or more poly-sulfated oligosaccharides from any structure related impurities; and
   (b) detecting and quantitating said poly-sulfated oligosaccharides in said sample, using a charged aerosol detector (CAD).

2. The method of claim 1, wherein the mobile phase used in the HILIC-UPLC column comprises a solvent and a salt.

3. The method of claim 2, wherein the salt is selected from ammonium formate, pyridinium formate and ammonium acetate.

4. The method of claim 3, wherein the salt is ammonium formate.

5. The method of claim 3, wherein the salt is ammonium formate and is present in the mobile phase at a concentration of from about 50 mM to 300 mM.

6. The method of claim 5, wherein the concentration of ammonium formate in the mobile phase is from about 100 mM to 200 mM.

7. The method of claim 2, wherein the solvent of the mobile phase used in the HILIC-UPLC column is acetonitrile, acetone or a mixture of acetonitrile and acetone.

8. The method of claim 2, wherein the solvent of the mobile phase used in the HILIC-UPLC column is acetonitrile.

9. The method of claim 1, wherein the poly-sulfated oligosaccharide is fondaparinux having the structure:

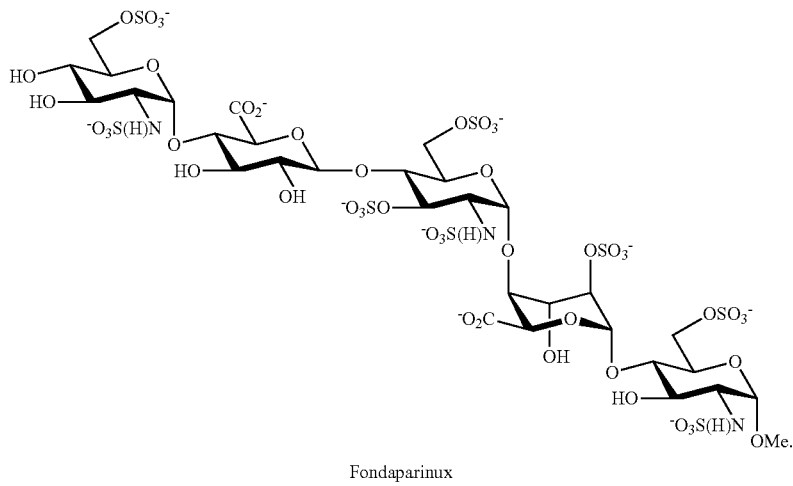

Fondaparinux

10. A method for detecting and quantitating fondaparinux in a sample, the method comprising:
   (a) subjecting said sample to chromatography on a hydrophilic interaction ultra-performance liquid chromatography (HILIC-UPLC) column having an amide-bonded stationary phase and a mobile phase, to separate fondaparinux from any structure related impurities, wherein the mobile phase used in the HILIC-UPLC column is acetonitrile, and the mobile phase comprises ammonium formate in a concentration of from about 100 mM to about 200 mM;
   (b) detecting and quantitating fondaparinux in said sample, using a charged aerosol detector (CAD).

* * * * *